United States Patent
Rowlen et al.

(10) Patent No.: US 6,377,341 B1
(45) Date of Patent: Apr. 23, 2002

(54) REFRACTIVE INDEX BASED DETECTOR SYSTEM FOR LIQUID CHROMATOGRAPHY

(75) Inventors: Kathy L. Rowlen, Longmont; Sarah G. Westerbuhr, Boulder, both of CO (US)

(73) Assignee: University Technology Corporation, Boulder, CO (US)

( * ) Notice: Subject to any disclaimer, the term of this patent is extended or adjusted under 35 U.S.C. 154(b) by 0 days.

(21) Appl. No.: 09/368,310

(22) Filed: Aug. 3, 1999

(51) Int. Cl.[7] .............................................. G01N 21/41
(52) U.S. Cl. ...................................... 356/128; 356/344
(58) Field of Search ................................ 356/128, 344, 356/436, 440; 250/574

(56) References Cited

U.S. PATENT DOCUMENTS 3,499,712 A * 3/1970 Kottle et al. ................. 356/440
4,042,304 A    8/1977 Martin et al.

OTHER PUBLICATIONS

Brathwaite, A. et al., *Chromatographic Methods* 5th Ed., Blackie Academic and Professional, Glasgow, 1996, Chap. 6, Sections 6.5.5.6, 6.5.5.6.1.
Brumbaugh, E. et al., Molecular Sieve Studies of Interacting Protein Systems, Journal of Biological Chemistry vol. 243, No. 24, Issue Dec. 25, 1968 pp. 6315–6324.
Rowlen, K. et al., Measurment of Column Efficiency, Analytical Chemistry, 1991, vol. 63 No. 6, pp. 575–579.
Rowlen, K. et al., Whole Column Detection, Analytical Chemistry vol. 61 No. 23, Dec. 1989, pp. 2624–2630.
Valkai, S. et al., Temperature Dependence of the Refractive Index, J.Chem. Thermodynamics 1998, vol. 30, pp. 825–832.
Schiebener, P. et al.Refractive Index of Water and Steam, J.Phys.Chem.Ref.Data, vol. 19 No. 3, 1990 pp. 677–715.
Lide, D.R.,ed. *CRC Handbook of Chemistry and Physics*, 73rd ed., CRC Press, Boca Raton, 1992 pp. 8–49.
Jones, M. et al., Scanning Gel Chromatography, Biophysical Chemistry 5, Mar. 1976, pp. 327–337.
Grothusen, J. et al., A Simple Method of Analyzing Profiles, Biophysical Chemistry 20, Elsevier, May 1984, pp. 299–304.
Broyles, B. et al., Visualization of viscous fingering, Journal of Chromatography A, 822, Jul. 1998, pp. 173–187.
Shalliker, R. et al., Visualization of solute migration, Journal of Chromatography A, 826, Sep. 1998, pp. 1–13.

* cited by examiner

*Primary Examiner*—Richard A. Rosenberger
(74) *Attorney, Agent, or Firm*—Emery L. Tracy

(57) ABSTRACT

An apparatus and method for on-column analysis in flash chromatography. The detection scheme utilizes refractive index changes as analytes move through an illuminated region of a chromatography column. The column packing material is a diffuse scattering medium when the refractive index of the solvent is significantly different than that of the packing material. The magnitude of the signal depends on the degree to which the refractive index mismatch is changed as an analyte passes through the illuminated region. This detection scheme provides a simple, inexpensive means for monitoring the end of a flash chromatography column to determine the exit time of the species of interest, thus greatly reducing the post-column analysis time. Additionally, the detector is movable along the length of the column, offering the potential to monitor separations as they occur.

35 Claims, 4 Drawing Sheets

REFRACTIVE INDEX BASED DETECTOR SYSTEM FOR LIQUID CHROMATOGRAPHY

BACKGROUND OF THE INVENTION

1. Field of the Invention

The present invention is related generally to detectors for use in liquid chromatography, and more particularly to an on-column detector utilizing variations in intensity of scattered light in the column arising from variations in the eluent refractive index as the eluent passes through the column.

2. Description of Related Art

Flash and gravity-fed chromatography are simple, commonly used preparative techniques for the separation of liquids, such as might be found in chemical reaction mixtures. A hollow column is packed with a solid particulate material, and a liquid eluent containing two or more components is caused to flow through the column. Gravity and/or compressed air may be used to enhance the flow rate. As the solution flows through the column, the components are differentially adsorbed onto and released from the particle surfaces, resulting in separation of the components from each other. Different volume fractions of the eluent can be collected after they exit the column, with each volume fraction enriched in one or more components and depleted in the other components relative to the eluent that enters the column.

The particulate packing material is selected to have different binding affinities for the solvent and the different dissolved species. Common packing materials include particles of silica gel or alumina. A typical particle size for silica gel is 60–200 mesh, or 75–250 $\mu$m diameter.

Frequently, glass columns are used for flash chromatography. The glass column containing the packing material allows for visualization of colored compounds as they are eluted from the column. However, because most separations involve non-colored compounds, products are typically isolated by collecting numerous fractions after the eluent exits the column and analyzing the fractions. Post-column analysis usually involves tedious evaluation of often more than a dozen fractions by thin layer chromatography.

SUMMARY OF THE INVENTION

It is an object of the present invention to provide an apparatus and method for monitoring a chromatography column to provide the operator with the information necessary to collect only eluent fractions that contain compounds of interest.

It is another object of the present invention to provide an easily portable apparatus for monitoring a chromatography column.

It is yet another object of the present invention to provide an apparatus and method for monitoring a chromatography column wherein the apparatus and method are useful with a wide range of compounds, including compounds that are substantially non-absorbing over the range of visible wavelengths.

It is still another object of the present invention to provide an apparatus and method for monitoring a chromatography column that are useful over a wide range of separation conditions. It is a further object of the present invention to provide an apparatus and method for monitoring a chromatography column that are useful over a wide range of column sizes.

It is yet a furher object of the present invention to provide an apparatus and method for monitoring a chromatography column that is inexpensive to construct.

It is still a further object of the present invention to provide an apparatus and method for monitoring a chromatography column that is simple to use.

To achieve the foregoing and other objects and in accordance with the purpose of the present invention broadly described herein, one embodiment of this invention comprises an apparatus for detecting liquids in a chromatography column which contains a stationary solid chromatography packing material and a liquid eluent. The apparatus comprises a light source positioned adjacent to the column and a light detector positioned adjacent to the column. The detector is substantially coplanar with and spaced apart radially from the light source, and the detector is responsive to changes in the intensity of light emanating from the source and scattered by the packing material in the column. The changes in light intensity may be caused by changes in the refractive index of the liquid eluent. The source and detector may be positioned at substantially the same height on the column and spaced apart radially at an angle between about 0 and about 180 degrees, preferably between about 90 and about 180 degrees. The light emanating from the source is substantially monochromatic, and the detector is capable of detecting light at the wavelength produced by the source. Preferably, the light source is a laser, and the detector is a photodiode. The apparatus is suitable for use with forms of liquid chromatograpy where the packing material scatters light. The apparatus is particularly suitable for use in monitoring flash chromatography and gravity-fed chromatograpy. Multiple detectors may be used with a single light source, spaced apart radially from each other. Also, one or more additional combinations of a light source and a detector may be positioned along the column.

Another embodiment of the present invention comprises an apparatus for detecting fluids in a chromatography column which contains a stationary solid chromatography packing material and a liquid eluent. The apparatus comprises a light source positioned adjacent to the column and a means for detecting variations in light scattered by the packing material as the fluid solution passes through the column. The amount of light scattered depends upon the difference between the refractive index of an eluent and the packing material. Preferably, the means for detecting light variations is a photodiode detector. The apparatus may also comprise means for collecting and storing data relating to the detected variations in light, such as an analog-to-digital converter and a microprocessor or a computer. In addition, some light variations may be due to light absorption by the eluent.

In yet another embodiment, the present invention comprises a method for detecting the presence of a liquid eluent in a chromatography column containing a stationary solid particulate chromatography packing material. The method comprises measuring the variations in the intensity of light scattered by the packing material. The variations in light intensity may be caused by variations in the refractive index of the eluent. The variations in light intensity may be measured using a light source and a detector positioned adjacent to the column, and the light source and the detector are spaced apart radially from each other, and the source and the detector may be moved longitudinally along the column to monitor progress of the eluent inside the column. Measurements may be made at a plurality of locations adjacent to the column, possibly using multiple light sources and detectors spaced along the column, with each detector spaced apart radially from a light source. The method may comprise the additional step of monitoring variations in the intensity of the scattered light over a time interval. The light should be substantially monochromatic and, preferably, the liquid, the column, and the packing material are substantially transparent to light at the wavelength produced by the source. Also preferably, the light has a wavelength in the visible range.

BRIEF DESCRIPTION OF THE DRAWINGS

These and other features, aspects, and advantages of the present invention will become better understood with reference to the following description, appended claims, and accompanying drawings, where:

DESCRIPTION OF THE INVENTION

Figure 1:
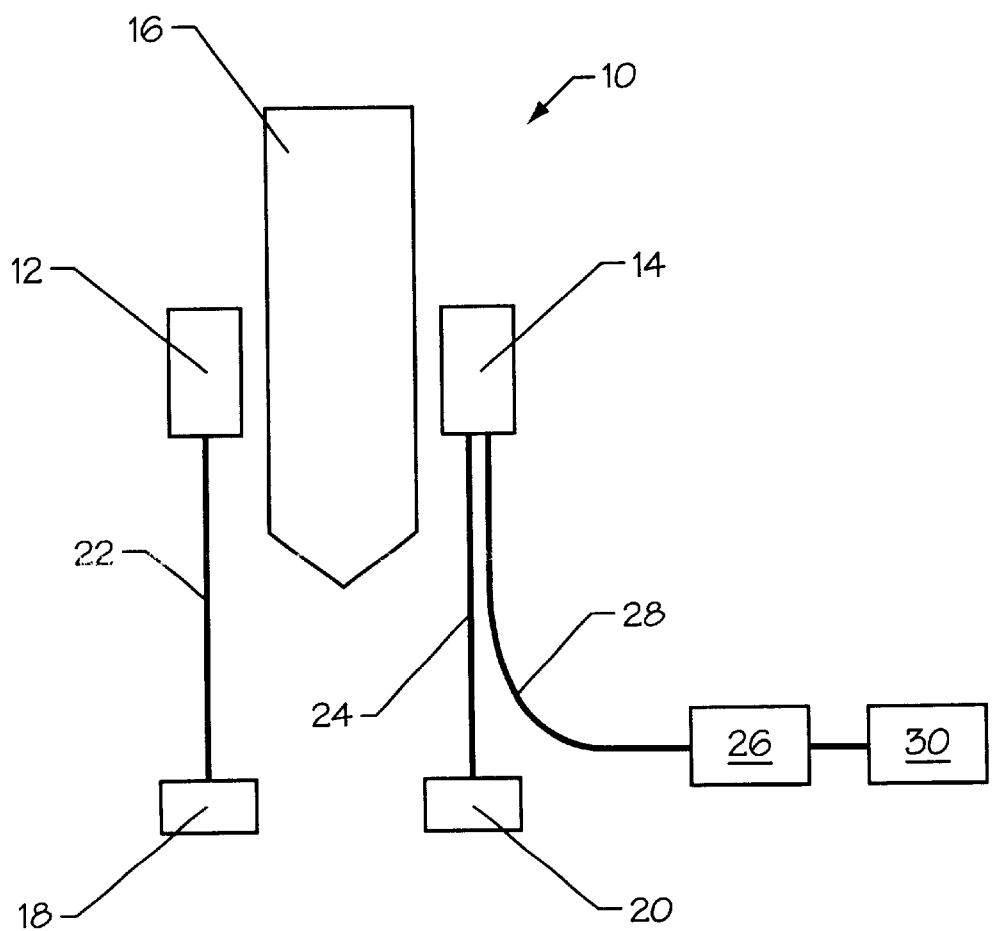
FIG. 1 is a schematic drawing of a detector system in accordance with the present invention.

On-column detection for preparative chromatography offers several advantages over conventional post-column detection methods, including the potential for automation of fraction collection. Multiple point on-column detection has been used to study column efficiency, capacity factors, and boundary profiles, as described in Broyles, B. S.; Shalliker, R. A.; Cherrak, D. E.; Guiochon, G. *J. Chromatogr. A* 1998, 822, 173–187; Shalliker, R. A.; Broyles, B. S.; Guiochon, G. *J. Chromatogr. A* 1998, 826, 1–13; Rowlen, K. L.; Duell, K. A.; Avery, J. P.; Birks, J. W. *Anal. Chem.* 1991, 63, 575–579; Rowlen, K. L.; Duell, K. A.; Avery, J. P.; Birks, J. W. *Anal. Chem.* 1989, 61, 2624–2630; Brumbaugh, E. E.; Ackers, G. K. *J. Biol. Chem.* 1968, 243, 6315–6324; Jones, M. M.; Harvey, G. A.; Ackers, G. K. *Biophys. Chem.* 1976, 5, 327–337; and Grothusen, J. R.; Zimmerman, J. K. *Biophys. Chem.* 1984, 20, 299–304, all of which are incorporated herein by refererence in their entirety.

In accordance with the present invention, a refractive index instrument can be mounted directly on a chromatography column at various positions along the column to monitor a chromatographic separation. The system in accordance with the present invention is simple to use and inexpensive. It can be used with a wide range of solvents and analytes, limited only by the conditions that the packing material and the solvent must be sufficiently transparent that light can be transmitted through the column, and that each analyte must have a different refractive index from the solvent.

The present invention relies on the observation that the packing materials used in liquid column chromatography frequently are particles of silica gel or alumina which are large enough to scatter visible light efficiently; a typical particle size for silica gel is 60–200 mesh, or 75–250 $\mu$m diameter. The magnitude and direction of light scattering by the particles in the column depend upon the refractive indices of the particles and the surrounding solution, as well as roughness features of the surfaces of the particles, as described in Hapke, B. *Theory of Reflectance and Emittance Spectroscopy;* Cambridge University Press: Cambridge, 1993, which is incorporated herein by reference in its entirety.

In accordance with the present invention, it has been found that the extent of light scattering through a packed column can be monitored to detect analytes. The magnitude of the signal is related to the degree to which the refractive index of the solvent, in combination with any dissolved analyte that may be present, matches that of the packing material. For example, if the refractive index of the solvent is significantly different than that of the particles, the light beam is diffusely scattered by the surfaces of the packing material particles. Conversely, if the refractive index of the solvent exactly matches the refractive index of the particles, non-absorbing particles appear to be transparent to a non-absorbed light beam traveling directly through the column. Because the signal is dependent primarily on the solvent's refractive index, a detector based on this approach can be used to detect most organic molecules and many dissolved inorganic species.

A schematic drawing of one embodiment of the present invention is shown in FIG. 1. The apparatus 10 comprises a light source 12 and a light detector 14. Source 12 and detector 14 are positioned adjacent to a chromatography column 16. Light source 12 and detector 14 are each connected to a light-weight power supply 18 and 20, respectively, via power cables 22 and 24, respectively, and detector 14 is also connected to an analog-to-digital converter 26 via data cable 28. Alternatively, a single power supply could be used to provide power for both the source 12 and the detector 14. Light source 12 should provide substantially monochromatic light which is, preferably, collimated and directed toward the column 16. The power and data cables 22, 24, and 28 may be sufficiently long to allow the source and detector to be separated physically from the power supplies and the analog-to-digital converter as required by the particular site where the instrument is used. For example, the column 16, light source 12, and detector 14 may be placed inside a fume hood, with the power supplies and the ananlog-to-digital converter in a more accessible location outside the fume hood. The analog-to-digital converter serves as an interface to a data collection and recording device 30, such as a personal computer or a simple microprocessor/display device. Any other suitable means of data collection and recording known in the art may be used. The apparatus may also include appropriate circuitry, as is known in the art, to stabilize the light source and the detector and to amplify the signal produced by the detector.

Figure 2A:
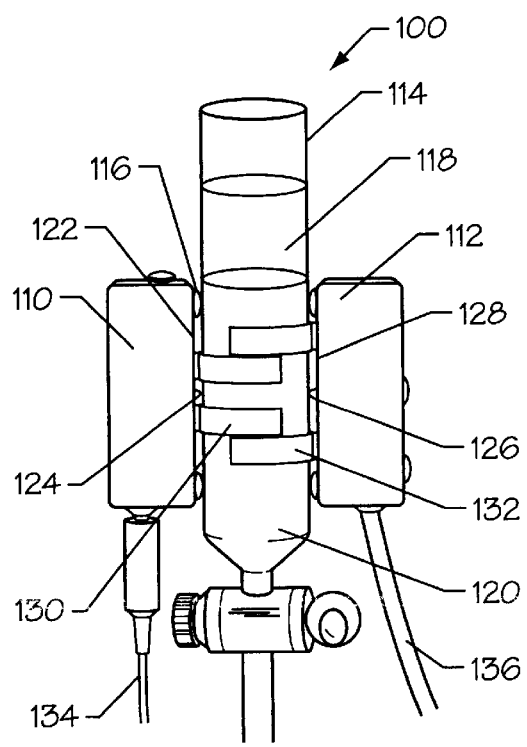
FIG. 2A is a digital photograph of an instrument in accordance with the present invention mounted onto a glass column packed with silica particles and filled with water.
Figure 2B:
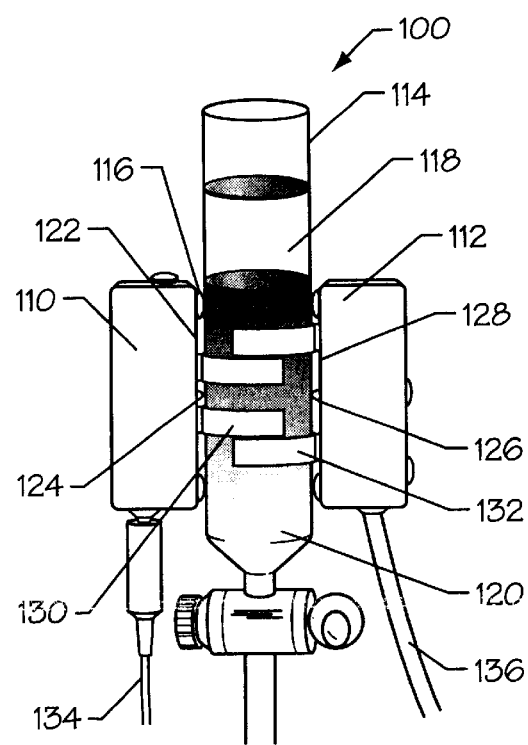
FIG. 2B is a digital photograph of the same instrument and column shown in FIG. 1a, but the solvent is chloroform.

FIGS. 2A and 2B are digital images of an apparatus 100 including the features shown in FIG. 1. The apparatus 100 comprises two compartments 110 and 112 housing a diode laser light source and a photodiode detector, respectively. As shown in FIG. 2, the compartments 110 and 112 are made from anodized aluminum and are identical in size; however, they could be made from any suitable material, and they could have different sizes. It should be noted that the compartments are not essential features of the invention.

They function to protect the light source and detector and to prevent stray light from reaching the detector. The compartments 110 and 112 are mounted to a short (10 cm) 2.5 cm diameter glass column 114 equipped with a stopcock 116. Although column 114 is a representative flash column, other size columns could be used. However, the column should be made of a material that is transparent to the wavelength of light used. Alternatively, the column could be provided with transparent windows at desired locations. The column 114, as shown in FIG. 2, is packed with silica gel 118 (60–200 mesh, Mallinckrodt, Paris, Ky.) supported on a plug of glass wool 120 at the stopcock 116. Compressed air may be used to force solvent through the column.

Compartment 110 has dimensions of 2.8 cm×2.2 cm×5.6 cm. Wall 122, adjacent to column 114, has a 0.2 cm diameter aperture 124, allowing the entire beam output by the laser to be transmitted to the column 114. Other aperture sizes could be used, depending on the cross section of the beam. The laser of the instrument shown in FIG. 2 has maximum emission at 660 nm and maximum power of 5 mW (Model #M6605 from NVG, Inc., Hazlehurst, Ga.) with a 3.3 V (±5%) power supply. A 660 nm laser source was chosen because it is inexpensive and light weight, and the wavelength is not likely to be absorbed by most organic molecules. However, any wavelength that is not strongly absorbed by either the column or the packing material could be used. Light having a wavelength in the visible range is preferred, because glass columns and many solvents and analytes do not absorb light significantly in the visible range. Many solvents and analytes absorb in the infrared and ultraviolet ranges, as does glass, which is commonly used for columns.

A 0.06 cm diameter aperture 126 in the wall 128 of the detector compartment 112 adjacent to the column 114 minimizes background light at the photodiode. A cut-off filter (not shown) may be used between the detector compartment and column to reduce background light. For example, the filter used in the instrument of FIG. 2 allows less than 0.1% transmission at 200–600 nm and 82.8% transmission at 660 nm. Preferably, the detector should detect light having wavelengths in the visible range to facilitate detection of a large number of analytes. A suitable photodiode detector, used in the instrument of FIG. 2, is manufactured by Hamamatsu, part number S1226-8BK. This photodiode has a 5 V±5% reverse bias and detects light from 320 to 1000 nm, with the peak sensitivity to light at approximately 660 nm. Other types of detectors, known in the art, could be used. The detector should be sensitive to light of the wavelength produced by the source.

The laser and detector compartments 110 and 112 are mounted onto the glass column 114 with metal clips 130 and 132, which can be made at the appropriate size for the column utilized or which can be made in a manner that allows the size to be changed easily. The clips 130 and 132 permit the laser and detector compartments 110 and 112 to be rotated around the column 114. The light source and detector can thus be positioned at any desired angle relative to each other, limited only by the sizes of the compartments, and both compartments may be moved up and down the length of the column. It should be noted that the light source and detector may be mounted directly onto a column by any other suitable means, or they may be positioned adjacent to the column. To maximize the amount of light detected through the aperture 126, compartments 112 and 114 should be positioned at approximately the same height on the column 114, as illustrated.

The laser is connected to a light-weight power supply, not shown, by power cable 134, and detector is connected to a light-weight power supply and to an analog-to-digital converter via power/data cable 136. The analog-to-digital converter serves as an interface to a personal computer, used for data collection. A suitable commercially available analog-to-digital converter is the Blue Earth Micro 485, available from Blue Earth Research, Mankato, Minn. Any other suitable means of data collection known in the art may be used, such as a simple microprocessor/display.

In the following discussion, $n_p$ refers to the refractive index of a particulate packing material, $n_s$ refers to the refractive index of a solvent, and $n_a$ refers to the refractive index of an analyte. The refractive index of various materials at 589.32 nm (sodium D line) is denoted $n_D$. The values of all refractive indices presented in the following discussion are $n_D$, taken from Lide, D. R., Editor *CRC Handbook of Chemistry and Physics,* 73rd Ed.; CRC Press: Boca Raton, 1992.

The following discussion refers to a number of chemicals. Ethyl acetoacetate (99+%) was obtained from Aldrich (Milwaukee, Wis.), and salicylic acid (Reagent Grade) was obtained from Matheson, Coleman, & Bell. Technical grade nickel chloride hexahydrate ($NiCl_2 \cdot 6H_2O$) was purchased from Fisher Scientific (Fair Lawn, N.J.). All other chemicals were ACS certified and obtained from Fisher Scientific (Pittsburgh, Pa.), with the exception of distilled water.

In the solvent based studies described below, a solvent was flushed through the packed column until a constant baseline was obtained, at which point the solvent was considered to be equilibrated with the column. An acceptable baseline exhibited a drift of $\leq 1\%$ over a 5 minute period and noise of $\leq \pm 3$ mV. When studying the instrument response to eluting analytes, the column was first equilibrated with the indicated solvent, followed by elution of the analyte by the solvent. Unless otherwise stated, the detection unit was positioned approximately 6 cm from the top of the column. This position was arbitrarily chosen; the detector unit may be positioned at any point along the length of the column. Although not always true for flash chromatography, it was noted that for the amounts of analyte loaded onto the column in this study, the peaks were generally Gaussian in shape. Therefore, peak areas and heights were obtained from Gaussian fits to the data using GRAMS/32 (ver. 4.01, Galactic Industries Corporation).

When the apparatus 100 is turned on, light from the source in compartment 110 passes through the aperture 124 and the packing material 118 in column 114 and is detected by the detector in compartment 112. The quantity of light scattered depends upon the difference between the refractive indices of the packing material and the solvent in the column. Therefore, the quantity of light detected is also a function of the difference between the refractive indices. Silica gel has a refractive index ($n_p$) of about 1.55. In FIG. 2A, the solvent is water ($n_s=1.333$), which leads to diffuse scattering of the beam. In FIG. 2B, the solvent is chloroform ($n_s=1.446$), which leads to forward scattering; in fact, only a small portion of light scattered at the glass interface can be seen on the right side of the column. The solvent may include one or more dissolved analytes which are passing through the column, so the refractive index of the solvent and the detected light intensity may vary as a fumction of quantity of the analyte or analytes present.

If desired, the photodiode response can be calibrated by attenuating the beam to varying degrees through solutions of an absorbing dye, such as green food coloring, placed in a glass cuvette. The detector signal in mV can be measured as a function of the percent transmission (% T) for each solution. The amount of light reaching the detector can be estimated from the % T of the solution, the laser spot size (assuming uniform intensity), the amount of light lost at the glass cuvette surfaces (4% per surface), and the detector aperture size.

To quantify the amount of light that actually passed through the center of the column 114 and not around the glass edges, a 5.0 mL volume of an optically thick dye (green food coloring) was eluted through the column with water. The undiluted dye had a transmittance of 0.013% T at 660 nm. The signal obtained with the dye moving through the detection zone was 9 mV. The dark noise was measured to be 7±1 mV; therefore only 2 mV can be attributed to light reaching the detector. The signal was plotted as a function of mW of light reaching the detector to provide a calibration curve for the detector. Based on the calibration curve, it was estimated that 2 mV corresponds to 0.4% of light reaching the detector without passing through the column for a typical 0.5 V signal. Because the observed signals, such as those in FIGS. 3–7, are generally in the range of tenths of a volt to several volts, it is unlikely that the signal is affected significantly by light scattering around the glass edges rather than through the column bed.

Figure 3:
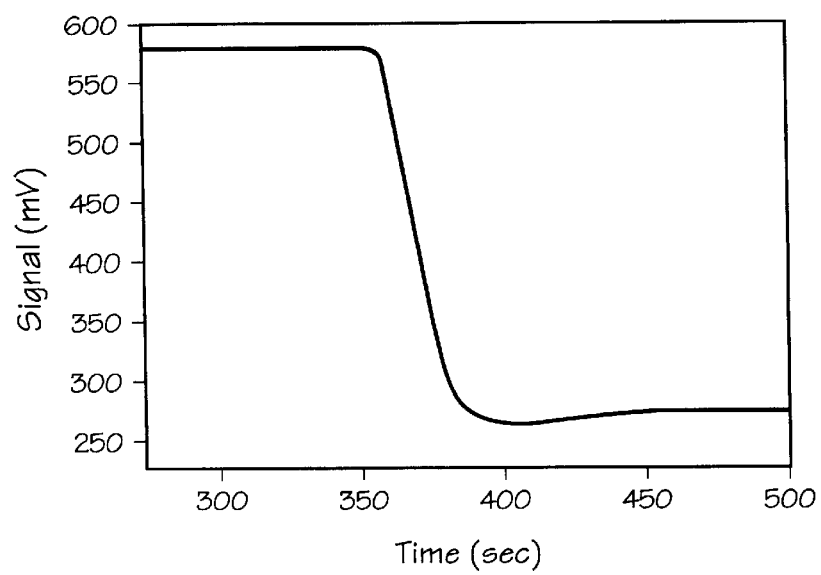
FIG. 3 is a graph showing the signal intensity as a function of time for the instrument shown in FIG. 1 as the solvent changes from ethyl acetate to methanol.

The amount of light exiting the column at any angle from the source direction is dependent on the refractive index of both the packing material and the solvent or solution between the light source and the detector, so the magnitude of the baseline signal depends on the solvent used. As an example, the change in signal when the solvent was switched from ethyl acetate to methanol is shown in FIG. 3, with the source and detector positioned 180 degrees apart from each other, as illustrated in FIG. 2. The detector signal is defined as the baseline voltage achieved once the column is equilibrated with solvent. The detector signal decreases by ~300 mV as methanol displaces ethyl acetate in the column. This behavior can be rationalized by considering that the refractive index of ethyl acetate ($n_s$=1.370) more closely matches that of the silica ($n_p$~1.55) than the refractive index of methanol ($n_s$=1.326) does.

Figure 4:
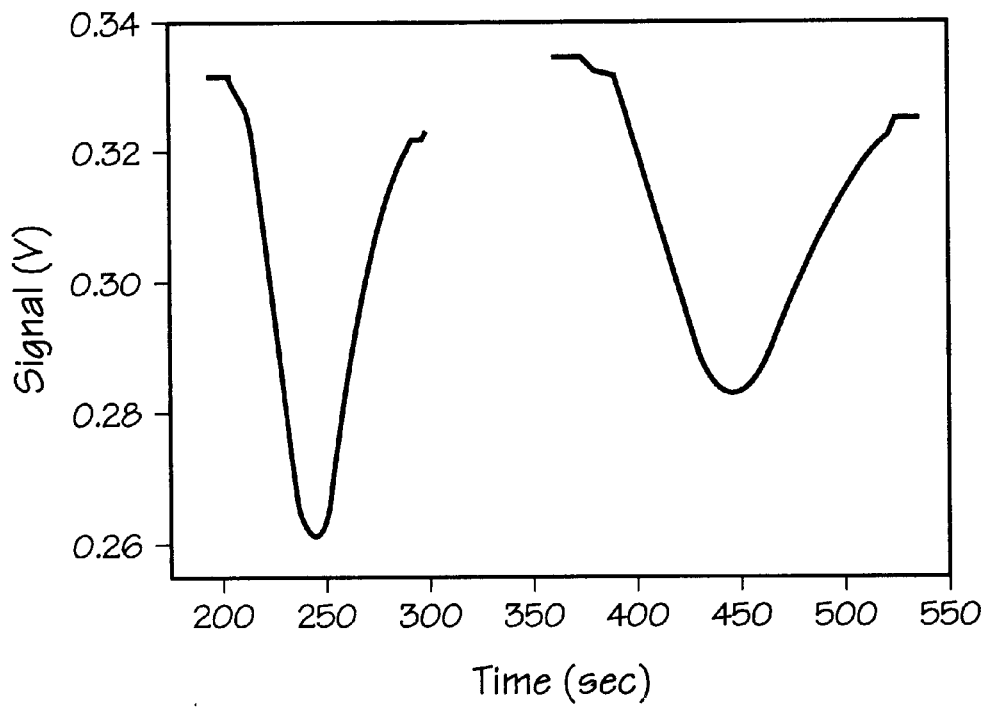
FIG. 4 is a graph showing the signal intensity vs time for 120 mg of $NiCl_2 \cdot 6H_2O$ (%T =3%) eluted with water for two source/detector positions on the column.

The 180 degree source/detector geometry can also be used to detect absorbance of an analyte. Nickel chloride hexahydrate ($NiCl_2 \cdot 6H_2O$) was chosen as a model absorbing analyte. A 0.25 M solution in water had an absorption of 0.4552 at 660 nm. Absorbance measurements were made with an HP model 8452A Diode Array Spectrometer (Hewlett-Packard, Wilmington, Del.). 120 mg of $NiCl_2 \cdot 6H_2O$(% T≈3%) was eluted in a column with water. The chromatographic peaks detected in the column are shown in FIG. 4. In this case, the signal reaching the detector decreased due to absorption of the light beam, indicated by the inverted peaks. The inverted peak on the left was monitored with the source and detector positioned 2 cm from the top of the column and the inverted peak on the right with the source and detector positioned at 6 cm from the top.

The magnitude of the baseline signal also depends on the source/detector geometry. To determine the excitation/detection geometry that resulted in the largest change in signal for a given mismatch in refractive index, the magnitude of the signal was measured with the detector at 90 degrees, 180 degrees, and at 10 degree intervals between 90 and 180 degrees. Various solvents were flushed through the column.

Figure 5:
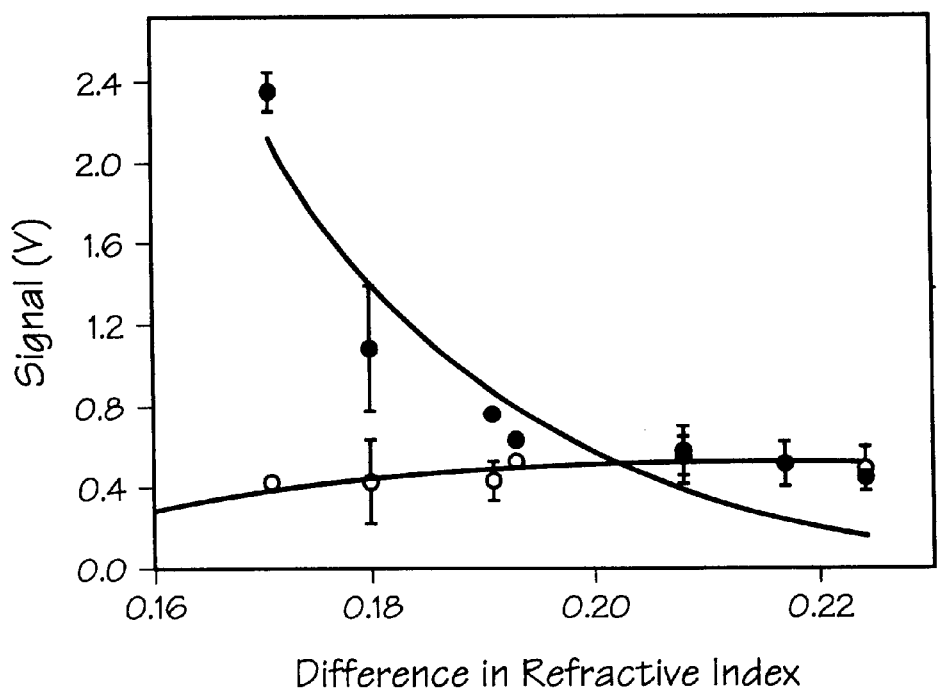
FIG. 5 is a graph of signal intensity as a function of the difference in refractive index between the packing material and the solvent surrounding the packing material in a column for seven solvents and source/detector geometries of 90 and 180 degrees.

The signal was monitored with the detector and laser positioned in a 90 degree geometry and a 180 degree geometry for nine different solvents. FIG. 5 shows the measured trend in signal as a function of the difference in $n_D$ for the silica and solvent for both the 90 degree (open circles) and 180 degree (filled circles) geometries. The seven data points, from left-to-right, correspond to the following solvents: hexanes, ethyl acetate, ethanol, acetone, acetonitrile, water and methanol. Two additional solvents, chloroform and ethyl acetoacetate matched the packing material's refractive index well enough to saturate the detector. As the refractive index of the solvent approached that of the silica, the signal for the 90 degree geometry decreased slightly while the signal for the 180 degree geometry increased dramatically. Thus, the 180 degree geometry was found to be more sensitive to changes in the solvent refractive index.

The data in FIG. 5 suggest two specific scattering regimes: one in which the refractive index mismatch is large and the particles are a diffusely scattering, or Lambert surface, (Hapke, B. *Theory of Reflectance and Emittance Spectroscopy;* Cambridge University Press: Cambridge, 1993, incorporated herein by reference in its entirety), and another in which the refractive index mismatch is small and light is scattered primarily in the forward direction. These extreme cases are demonstrated in FIG. 3; the solvent in (A) is water ($n_s$=1.333) and the solvent in (B) is chloroform ($n_s$=1.446). One would predict an intermediate case in which the light is scattered nearly isotropically.

Further evidence for the transition between two distinct scattering conditions, diffuse and forward, was obtained by probing the angular dependence of the scattering signal. By systematically varying the angle between the source and detector (between 90 and 180 degrees), the angular dependence of scattering was mapped out for three solvents, water, acetonitrile, and ethyl acetate. As observed in FIG. 6, for the larger refractive index mismatch between the solvent and packing material (water as solvent, $n_s$=1.333, open squares) the detector signal is largest in the 90 degree geometry and decreases as the detector is positioned in the forward scattering direction. At an intermediate mismatch in refractive index (acetonitrile, $n_s$=1.342, open circles) the signal is reasonably constant at all angles, suggesting isotropic scattering (at least in the forward hemisphere). With a better match between the solvent (ethyl acetate, $n_s$=1.370, filled circles) and packing material, the signal increases as the detector is moved from the 90 degree geometry to the 180 degree geometry, suggesting primarily forward scattering. The range for 2 measurements represents the variation due to repositioning the detector and laser compartments on the column. The average relative error associated with removal of the instrument and repacking the column is much higher (on the order of 20%). Such large error is associated with variables such as repacking the column, readjusting the source and detector, and variability in the laser power.

Figure 6:
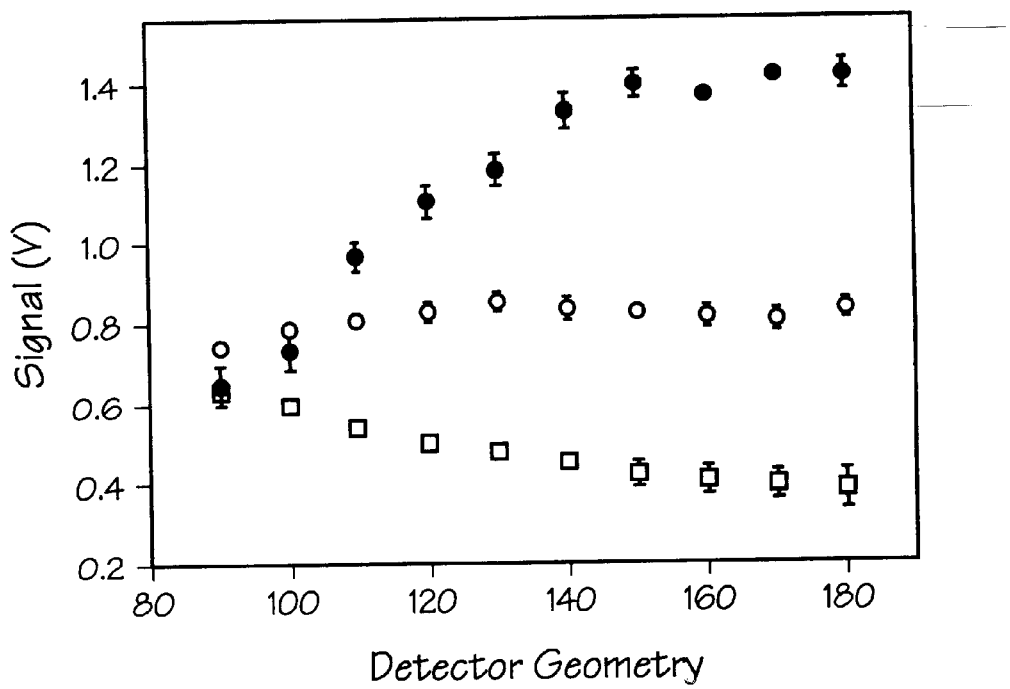
FIG. 6 is a graph showing the signal intensity as a function of the angle between the source and detector for ethyl acetate (filled circles), acetonitrile (open circles), and water (open squares)

As indicated in both FIGS. 5 and 6, the cross-over refractive index for the two scattering conditions appears to be ~1.34. For this particular system, 1.34 is the solvent refractive index for which light is scattered equally at both 90 degrees and 180 degrees from the source.

To better understand the observed trends in signal as a function of solvent/analyte refractive index, studies were conducted to develop an empirical model that qualitatively describes the observed trends.

The peak height was measured as a function of analyte mass for a non-absorbing analyte, ethyl acetoacetate, to determine the concentration response. The detector response was monitored at the same position on the column and therefore in the same volume. (Rowlen, K. L.; Duell, K. A.; Avery, J. P.; Birks, J. W. *Anal. Chem.* 1991, 63, 575–579.)

Figure 7:
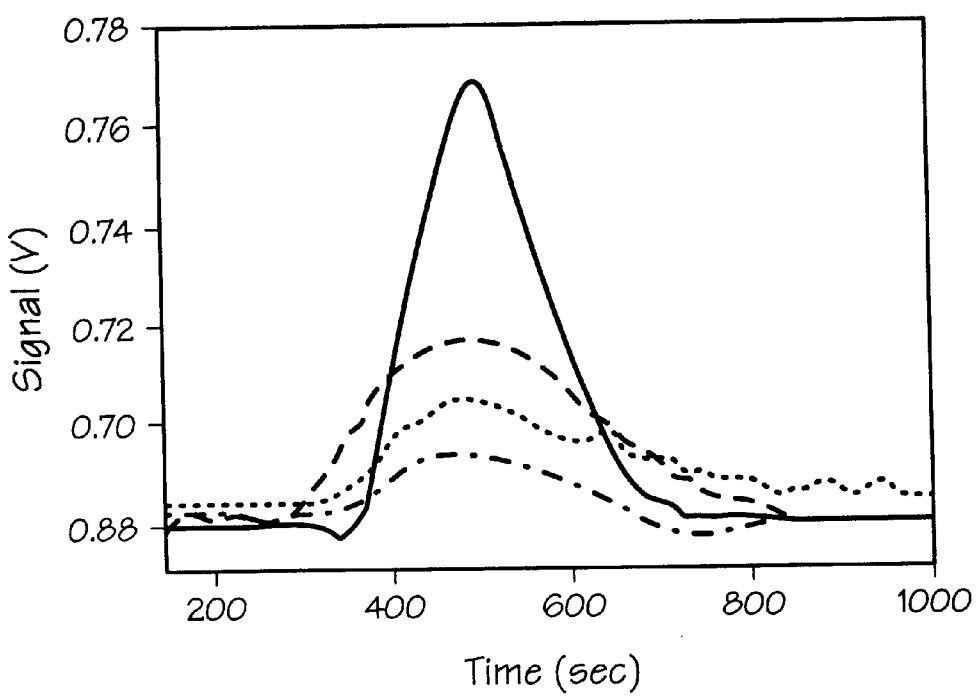
FIG. 7 is a graph containing sample chromatograms for ethyl acetoacetate eluted with ethyl acetate, wherein the various curves correspond to different quantities of ethyl acetoacetate added to the top of the column.

FIG. 7 shows the transient peaks as the ethyl acetoacetate was eluted with ethyl acetate and passed through the detection zone; each has been shifted to an arbitrary time for the signal maximum. The various curves correspond to different quantities of ethyl acetoacetate added to the top of the column; from largest peak to smallest, the quantities of ethyl acetoacetate were 510.5 mg, 408.4 mg, 204.2 mg, and 102.1 mg, respectively. The source and detector were in a 180 degree geometry as shown in FIG. 2. As expected for flash chromatography, the peaks are broad.

It should be noted that for the anticipated application of the detector system of the present invention—monitoring near the end of the column in order to predict the exit time of a compound—it is important to have a qualitative understanding of the minimum amount of analyte detectable. However, quantitatative measurements of the analyte mass are not generally needed. As discussed in detail later, the sensitivity, or change in signal as a function of change in analyte concentration, is dependent on the refractive index of all three components, the packing material, the solvent, and the analyte, and may therefore be specified for only a particular system.

The lowest detected amounts for representative combinations of solvents and analytes are summarized in Table I. The limit of detection is approximately 20 mg for the specific non-absorbing compounds investigated with the particular instrument illustrated in FIG. 2 and described above, (5 mW source, 2.5 cm dia. silica-packed column). It is anticipated that tens of milligrams is a representative number, because the solvents listed in Table I are conunonly used for flash chromatography, and the analytes are representative. As summarized in Table I, the calibration curves are reasonably linear but do exhibit a slight degree of curvature.

laser power reaching the detector. For comparison, the detector exhibited a response of ~4 V/$\mu$W at higher light fluxes.

The influence of several additional parameters on the results was considered. These parameters include the monitoring of materials at a wavelength other than the wavelength for which refractive indices ($n_D$) are reported in the literature, as well as temperature and pressure effects on refractive index.

The reported refractive indices ($n_D$) are strictly valid only at 589.32 nm. However, the refractive indices at the wavelength of interest here (660 nm) should be very similar to $n_D$. For example, the refractive indices for water and chloroform at 660 nm differ from those at 589 nm by less than 0.5%. See Schiebener, P.; Straub, J.; Levelt Sengers, J. M. H.; Gallagher, J. S. *J. Phys. Chem. Ref. Data* 1990, 19, 677–715; and Valkai, S.; Liszi, J.; Szalai, I. *J. Chem. Thernodyn.* 1998, 30, 825–832, which are incorporated herein by reference.

Thermal fluctuations leading to fluctuations in the refractive index are well known to pose the primary limit to sensitive detection in standard refractive index detectors. The general rule is that the refractive index of an organic liquid changes by $4 \times 10^{-4}$ units per degree. See, for example, Braithwaite, A.; Smith, F. J. *Chromatographic Methods*, 5$^{th}$ ed.; Blackie Academic and Professional: Glasgow, 1996; Chapter 6, which is incorporated herein by reference in its entirety. Because the instrument presented here in accordance with the present invention was designed for relatively high quantities of analyte (mg), normal laboratory temperature fluctuations were tolerable, and no temperature control was necessary. If the present invention were used in settings where the temperature differed significantly from ambient laboratory temperature, the refractive index variations attrib-

TABLE I

Summary of Analyte Response Data

| Analyte | $n_a$ | Solvent | $n_s$ | Mass Range Investigated (mg) | Slope ± σ mV (peak height)/ g analyte | R[c] | LDA (mg)[c] | S/N[c] |
|---|---|---|---|---|---|---|---|---|
| salicylic acid | 1.565 | ethyl acetate | 1.370 | 14–240 | 0.47 ± 0.06 | 0.973 | 14 | 7 |
| ethyl acetoacetate | 1.419 | ethyl acetate | 1.370 | 20–510 | 0.12 ± 0.02 | 0.887 | 20 | 4.2 |
|  |  |  |  |  | 0.066 ± 0.005[a] | 0.984 |  |  |
| ethyl acetoacetate | 1.419 | methanol | 1.326 | 20–1020 | 0.088 ± 0.006[b] | 0.978 | 20 | 2.5 |
| nickle chloride | — | water | 1.333 | 2–60 | — | — | 2.4 | 2.5 |

[a]Linear regression data if the highest concentration point is not included in fit. When peak area was used instead of peak height, the linear regression fits were poorer, but the trands were similar to those for peak height.
[b]From the average of two independent data sets.
[c]Where the slope is based on a linear regression to the signal versus grams data, R is the correlation coefficient, LDA is lowest detected amount, and S/N is the signal to noise ratio based on peak height and the 0.5 average peak-to-peak noise in the background.

It should be noted that, for applications such as flash chromatography, the sensitivity of the detector system may not be a critical issue because samples are often greater than milligram quantities. Once the system is set up with a light source having a suitable intensity, suitable aperture sizes, a suitable detector, and, if desired, suitable filters for a particular type and size of column and particular solvents and analytes used, the system does not need to be calibrated for each use to obtain qualitative results.

The limit of detection can be significantly improved over that indicated in Table I by optimizing the detector sensitivity. For the estimated light flux regime used in these studies, the photodiode had a response of ~0.7 V per $\mu$W of utable to temperature fluctuations should be minimal during a separation procedure conducted, if the separation is equilibrated to a given temperature.

Flash chromatography typically utilizes compressed air to speed up the flow of solvent through the column. While there are fluctuations in the pressure applied to the column during the course of a separation, the magnitude of the these pressure fluctuations results in negligible changes in refractive index of the solvent; the coefficient for refractive index changes is $4 \times 10^{-5}$ per atmosphere. See, for example, Braithwaite, A.; Smith, F. J. *Chromatographic Methods*, 5$^{th}$ ed.; Blackie Academic and Professional: Glasgow, 1996; Chapter 6. However, the packing density of the stationary phase is more susceptible to changing pressure. Poorly packed columns, as determined by visual inspection, were sensitive to a change in pressure. For example, when the pressure was alternated between atmospheric and a pressure sufficient to forcefully disjoin a lid from the column, the signal permanently changed by as much as 11 mV. For a visually well packed column, the signal spiked up to 11 mV when the air flow was first applied, but returned to the baseline signal of ±3 mV within about 1 second. Compared to the 11 mV spike associated with an abrupt pressure change, the signal observed for an analyte near the limit of detection would have a similar change in the magnitude of the signal, but the peak would last for at least 30 seconds. Therefore, pressure changes are not likely to yield false positive peak detection.

The detector system may be positioned at any point along the length of the column, as indicated by the data in FIG. 4, and used to monitor the progress of a separation as one or more analytes pass the source and detector. In addition, the progress of the separation may be monitored by periodically repositioning the detection unit or by using multiple units spaced along the column. As expected due to broadening of an analyte band as it travels along the column, the peak width is narrower near the top of the column than near the bottom.

An apparatus according to the present invention, such as the apparatus shown in FIG. 2, is easily portable and can be constructed inexpensively from commercially available components. This type of apparatus can be used for monitoring chromatography columns of a wide range of sizes, with appropriate light source intensities and detector sensitivities. It can be used to monitor separations of a wide variety of liquids over a wide range of separation conditions. Also in accordance with the present invention, the system can be used to identify a liquid eluent having a predetermined composition by monitoring the signal until a detector response is observed that corresponds to the expected response for a liquid having the refractive index of the predetermined composition and passing through the illuminated region of the column.

The foregoing description is considered as illustrative only of the principles of the invention. Further, since numerous modifications and changes will readily occur to those skilled in the art, it is not desired to limit the invention to the exact construction and process shown as described above. Accordingly, all suitable modifications and equivalents may be resorted to falling within the scope of the invention.

We claim:

1. An apparatus for detecting analytes in a chromatography column, the column containing a stationary solid chromatography packing material and a liquid eluent, the apparatus comprising:
   a light source positioned adjacent to the column; and
   a light detector positioned adjacent to the column, wherein the detector is substantially coplanar with and spaced apart radially from the light source, wherein the detector is responsive to changes in the intensity of light emanating from the source and scattered by the packing material in the column and measures radiation intensity variations due to differences between the refractive index of the packing material/liquid eluent and the analyte;
   wherein the measured signal is inversely related to the refractive index difference.

2. The apparatus of claim 1, wherein the light is substantially monochromatic.

3. The apparatus of claim 2, wherein the light has a wavelength in the visible range.

4. The apparatus of claim 1, wherein the light source is contained in a compartment, and the compartment includes an aperture between the light source and the column.

5. The apparatus of claim 1, wherein the detector is contained in a compartment, and the compartment includes an aperture between the column and the detector.

6. The apparatus of claim 1, additionally comprising a wavelength filter between the light source and the detector.

7. The apparatus of claim 1, wherein the changes in light intensity reaching the detector are caused by changes in the refractive index of the liquid eluent.

8. The apparatus of claim 1, wherein the source and the detector are positioned on the column.

9. The apparatus of claim 1, wherein the column is a flash chromatography column or a gravity-fed chromatography column.

10. The apparatus of claim 1, wherein the liquid eluent is substantially transparent to light of a wavelength emitted by the source and detected by the detector.

11. The apparatus of claim 1, wherein the column and the packing material are substantially transparent to light at a wavelength emitted by the source.

12. The apparatus of claim 1, wherein the detector is a photodiode detector.

13. The apparatus of claim 1, wherein the light source is a laser.

14. The apparatus of claim 1, wherein the light source and the light detector are spaced apart radially at an angle between about 90 degrees and about 180 degrees.

15. The apparatus of claim 1, further comprising:
   at least one additional light source positioned adjacent to the column; and
   at least one additional light detector corresponding to each additional light source and positioned adjacent to the column and spaced apart radially from the additional light source, wherein each detector is responsive to changes in the intensity of light emanating from the corresponding additional light source and scattered by the packing material in the column.

16. The apparatus of claim 1, further comprising:
   at least one additional light detector positioned adjacent to the column and spaced apart radially from the light source and the light detector in a substantially planar arrangement.

17. An apparatus for detecting analytes in a chromatography column containing a stationary solid chromatography packing material and a liquid eluent, the apparatus comprising:
   a light source positioned adjacent to the column; and
   means for detecting variations in light scattered by the packing material/liquid eluent/analyte as the fluid solution passes through the column, the means for detecting being positioned less than 180 degrees from the light source relative to the column.

18. The apparatus of claim 17, wherein the means for detecting is a photodiode detector.

19. The apparatus of claim 17, additionally comprising means for collecting and storing data relating to the detected variations in light.

20. The apparatus of claim 19, wherein the means for collecting and storing data comprises an analog-to-digital converter and a device selected from microprocessors and computers.

21. The apparatus of claim 17, wherein at least some of the variations in the scattered light are caused by variations in the refractive index of the eluent.

22. The apparatus of claim 17, wherein some of the variations in scattered light result from light absorption by the eluent.

23. A method for detecting the presence of an analyte in a chromatography column containing a stationary solid particulate chromatography packing material, the method comprising:

measuring the variations in the intensity of light scattered by the packing material/eluent/analyte combination that is inversely related to the difference in packing material/eluent and analyte refractive index.

24. The method of claim 23, wherein the liquid eluent has a predetermined composition.

25. The method of claim 23, wherein the variations in light intensity reaching the detector are caused by variations in the refractive index of the eluent.

26. The method of claim 23, wherein the measuring step comprises using a light source and a detector positioned adjacent to the column, and the light source and the detector are spaced apart radially from each other.

27. The method of claim 23, comprising the additional step of:

moving the source and detector longitudinally along the column to monitor progress of the eluent inside the column.

28. The method of claim 23, wherein the measuring step comprises:

measuring the variations in the intensity of light scattered by the packing material at a plurality of locations adjacent to the column.

29. The method of claim 28, wherein the measuring step comprises using a plurality of detectors positioned adjacent to the column in a substantially planar arrangement and spaced apart radially from each other.

30. The method of claim 28, wherein the measuring step comprises using a plurality of light sources and a plurality of light detectors, each detector corresponding to a light source and spaced apart radially from its corresponding light source, and the light sources are spaced apart from one another longitudinally along the column.

31. The method of claim 23, further comprising the step of monitoring variations in the intensity of the scattered light over a time interval.

32. The method of claim 23, wherein the liquid, the column, and the packing material are substantially transparent to light at a wavelength detected by detector.

33. The method of claim 32, wherein the wavelength is in the visible range.

34. The method of claim 23, wherein the variations in scattered light intensity are caused by variations in the refractive index of the eluent.

35. A system for column chromatography, comprising:

a chromatography column, the column containing a stationary solid chromatography packing material and a liquid eluent;

a substantially monochromatic light source positioned adjacent to the column; and a light detector positioned adjacent to the column, wherein the detector is substantially coplanar with and spaced apart radially with the light source at an angle less than 180 degrees relative to the column, wherein the detector is responsive to changes in the intensity of light emanating from the source and scattered by the packing material in the column.

* * * * *